United States Patent
Shinozaki et al.

(10) Patent No.: US 6,245,919 B1
(45) Date of Patent: Jun. 12, 2001

(54) CYCLOPROPYLGLYCINE DERIVATIVES AND AGONISTS FOR METABOTRONIC L-GLUTAMATE RECEPTORS

(75) Inventors: Haruhiko Shinozaki, 477-17-15-507, Konba-cho, Omiya-shi, Saitama; Takeo Taguchi, Tokyo; Michiko Ishida, Saitama, all of (JP)

(73) Assignees: Haruhiko Shinozaki, Saitama; Takeo Tagushi; Nippon Chemiphar Co., Ltd., both of Tokyo, all of (JP)

( * ) Notice: Subject to any disclaimer, the term of this patent is extended or adjusted under 35 U.S.C. 154(b) by 0 days.

(21) Appl. No.: 09/221,916

(22) Filed: Dec. 28, 1998

Related U.S. Application Data

(63) Continuation-in-part of application No. 09/214,108, filed on Dec. 28, 1998, now abandoned.

(30) Foreign Application Priority Data

Jun. 28, 1996 (JP) .................................................. 8-188520

(51) Int. Cl.$^7$ ...................... C07D 209/32; C07D 209/46; C07C 69/74; C07C 61/04; C07C 61/16
(52) U.S. Cl. ........................... 548/512; 560/124; 562/506
(58) Field of Search ........................... 548/512; 540/124; 562/506

(56) References Cited

FOREIGN PATENT DOCUMENTS

06024970 * 2/1994 (JP) .............................. A61K/31/195

OTHER PUBLICATIONS

Tetrahedron, vol. 52, No. 1, p271–278, 1996, Shibuya et al., 'A highly diastereoselective synthesis of trans-3,4-(difluoromethano)glutamic acid.'*

* cited by examiner

Primary Examiner—Johann Richter
Assistant Examiner—Brian J. Davis
(74) Attorney, Agent, or Firm—Reed Smith LLP

(57) ABSTRACT

A cyclopropylglycine derivative having the following formula:

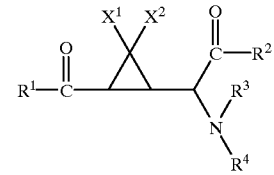

and an intermediate compound for the synthesis of the cyclopropylglycine derivative are novel compounds. The cyclopropylglycine derivative shows a selectivity higher than that of the known agonists to metabotropic L-glutamate receptors, and therefore is a metabotropic type agonist to L-glutamate which has excellent characteristics.

7 Claims, No Drawings

CYCLOPROPYLGLYCINE DERIVATIVES AND AGONISTS FOR METABOTRONIC L-GLUTAMATE RECEPTORS

This application is a CIP of application Ser. No. 09/214,108 filed Dec. 28, 1998 now abandoned.

FIELD OF THE INVENTION

This invention relates to novel cyclopropylglycine derivatives and an agonist comprising the derivative as an active compound. The agonist acts on metabotropic L-glutamate receptors.

BACKGROUND OF THE INVENTION

Glutamate receptors are roughly categorized into two types, namely, ionotropic type (iGluR) and metabotropic type (mGluR). The receptors of ionotropic type (iGluR) are further categorized into NMDA (N-methyl-D-aspartic acid) type and non-NMDA type [Jpn. J. Neuropsychopharmacol., 18(5), 345–365 (1996)].

When NMDA receptors are activated with agonists, they introduce calcium ions ($Ca^{2+}$) into cells to increase the intracellular $Ca^{2+}$ concentration. In the cells, accordingly, various $Ca^{2+}$-dependent enzymes are activated to cause a chain of cellular changes. If the cellular changes proceed over a certain threshold value, the cell is presumed to lose irreversibly its life [Folia Pharmacol. Jpn., No. 104, 177–187 (1994)].

The metabotropic L-glutamate receptors (mGluR) are classified into three groups (Groups-I, -II and -III) based on their sequence homology, intracellular signal transduction pathway, and selectivity of agonists for receptor sub-types. A typical example of the agonist for Group-I is quisqualic acid, which promotes formation of inositol triphosphate ($IP_3$) and variations of intracellular $Ca^{2+}$ dynamics.

The agonists for Group-II and Group-III inhibit intracellular CAMP formation induced by forskolin. In the agonist selectivity, the mGluR of Group-II differs from that of Group-III.

Examples of the agonists for mGluR of Group-II include DCG-IV [(2S,1'R,2'R,3'R)-2-(2,3-dicarboxycyclopropyl) glycine] and L-CCG-I [(2S,1'S,2'S)-2-(2-carboxycyclopropyl)glycine]. Examples of the agonists for mGlu R of Group-III include L-AP4 [L-2-amino-4-phosphonobutyric acid] [Japanese Patent Provisional Publications No. 6(1994)-256323 and No. 6(1994)-24970, and Jpn. J. Neuropsychopharmacol., 18(6), 419–425 (1996)].

The agonists for mGluR of Group-II are known to inhibit release of transmitter at synapses, and consequently to lower the efficiency of synaptic conduction. If the synaptic transmission efficiency is lowered in the central nervous system, the muscles in the kinetic system are presumed to be relaxed. Actually, it has been ascertained by experiments on animals that the agonists for mGluR of Group-II remarkably potentiate anesthesia. These agonists are also known to give sedation (or tranquilizer-like) effect and anti-epileptic effect. Further, since these agonists can protect the neurons cells from death in vivo and in vitro caused by excitatory amino acids, they are expected to be used as neuron protectors. Since the agonists for mGluR of Group-II are utterly new agonists for glutamate receptors and seem to be indispensable for pharmaceutical studies of the central nervous system, they are of great value as reagents for the laboratory study. [Folia Pharmacol. Jpn., No. 104, 177–187 (1994)].

DCG-IV (which is one of the known agonists for mGluR of Group-II) strongly activates the mGluR, and is hence expected to act as a neuron protector. However, since DCG-IV also activates NMDA receptors (which are presumed to be concerned with cell death caused by excitatory amino acids), it is desired to develop a new agonist for mGluR having no NMDA activating component.

SUMMARY OF THE INVENTION

It is an object of the present invention to provide a novel cyclopropylglycine derivative having better selectivity and characteristics than known agonists for glutamic acid receptors of metabolic regulation type.

It is another object of the invention to provide a new compound employable as an intermediate for preparing the novel cyclopropylglycine derivative.

This invention resides in a cyclopropylglycine derivative having the following formula (I).

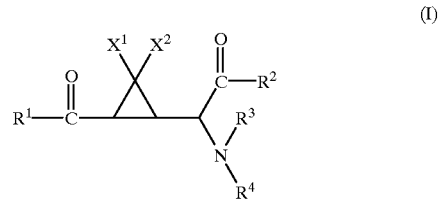

In the formula (I), each of $R^1$ and $R^2$ independently represents a hydroxyl group or an alkoxy group having 1 to 6 carbon atoms, each of $R^3$ and $R^4$ independently represents a hydrogen atom or an alkyl group having 1 to 6 carbon atoms, and each of $X^1$ and $X^2$ independently represents a halogen atom.

The invention also resides in an agonist which acts on L-glutamic acid receptors of metabolic regulation type and which comprises the cyclopropylglycine derivative having the formula (I) as an active component.

Further, the invention resides in a pharmaceutical composition comprising the cyclopropylglycine derivative having the formula (I) as an active component.

The intermediate provided by the invention is a lactam derivative having the following formula (II).

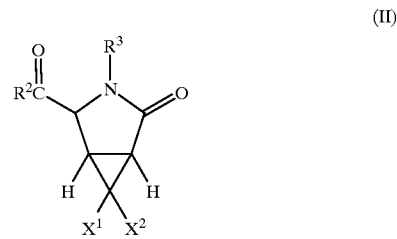

In the formula (II), $R^2$ represents a hydroxyl group or an alkoxy group having 1 to 6 carbon atoms, $R^3$ represents a hydrogen atom or an alkyl group having 1 to 6 carbon atoms, and each of $X^1$ and $X^2$ independently represents a halogen atom.

PREFERRED EMBODIMENTS OF THE INVENTION

The cyclopropylglycine derivative of the invention has the following formula (I):

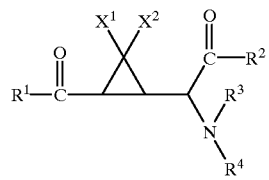

In the formula (I), each of $R^1$ and $R^2$ independently represents a hydroxyl group or an alkoxy group having 1 to 6 carbon atoms (e.g., methoxy, ethoxy, n-propoxy, isopropoxy, n-butoxy, and isobutoxy), each of $R^3$ and $R^4$ independently represents a hydrogen atom or an alkyl group having 1 to 6 carbon atoms (e.g., methyl, ethyl, n-propyl, isopropyl, n-butyl, and isobutyl), and each of $X^1$ and $X^2$ independently represents a halogen atom (e.g., fluorine, chlorine, bromine, and iodine).

The cyclopropylglycine derivative of the invention can be used in the form of a free acid or its salt. Preferably, in the formula (I), each of $R^1$ and $R^2$ represents a hydroxyl group, each of $R^3$ and $R^4$ represents a hydrogen atom, and each of $X^1$ and $X^2$ represents a fluorine atom. In other words, a preferred embodiment of the derivative is 2-(2'-carboxy-3',3'-difluoro)cyclopropylglycine. This compound has the following eight optical isomers.

L-I: (2S,1'S,2'S)-2-(2'-carboxy-3',3'-difluoro)-cyclopropylglycine,
L-II: (2S,1'R,2'R)-2-(2'-carboxy-3',3'-difluoro)-cyclopropylglycine,
L-III: (2S,1'S,2'R)-2-(2'-carboxy-3',3'-difluoro)-cyclopropylglycine,
L-IV: (2S,1'R,2'S)-2-(2'-carboxy-3',3'-difluoro)-cyclopropylglycine,
D-I: (2R,1'R,2'R)-2-(2'-carboxy-3',3'-difluoro)-cyclopropylglycine,
D-II: (2R,1'S,2'S)-2-(2'-carboxy-3',3'-difluoro)-cyclopropylglycine,
D-III: (2R,1'R,2'S)-2-(2'-carboxy-3',3'-difluoro)-cyclopropylglycine,
D-IV: (2R,1'S,2'R)-2-(2'-carboxy-3',3'-difluoro)-cyclopropylglycine, Most preferred is (2S,1'S,2'S)-2-(2'-carboxy-3',3'-difluoro)cyclopropylglycine [L-I].

The cyclopropylglycine derivative of the invention can be prepared in the manner shown in the following reaction scheme-1 and -2. In the reaction scheme-1, a known olefin compound [E-1 or Z-1; see J. Org. Chem., 59(1), 97–103 (1994)] is caused to react with sodium chlorodifluoroacetate to prepare two optical isomers of 2-(2'-benzyloxymethyl-3',3'-difluoro)cyclopropylethyleneglycol 1,2-O-acetonide [reaction from E-1 is described in Tetrahedron: Asymmetry, 5(8), 1423–1426(1994)]. From thus obtained compounds, the target cyclopropylglycine derivatives can be prepared in the manner shown in the reaction scheme-2. The reaction scheme-2 shows, for example, the reactions for preparing the derivatives of L-I and D-II.

Reaction scheme-1

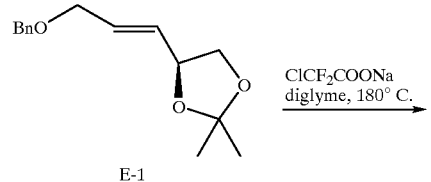

E-1

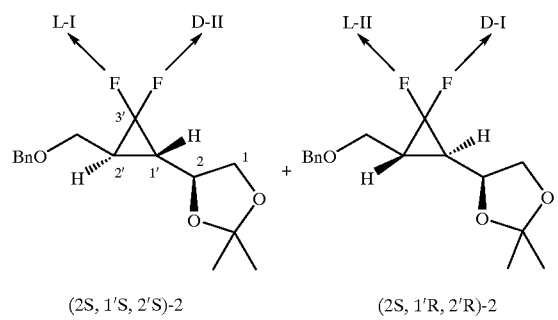

(2S, 1'S, 2'S)-2          (2S, 1'R, 2'R)-2

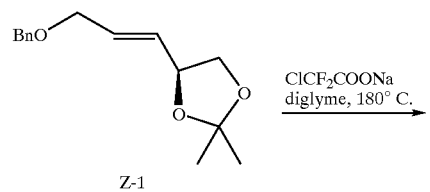

Z-1

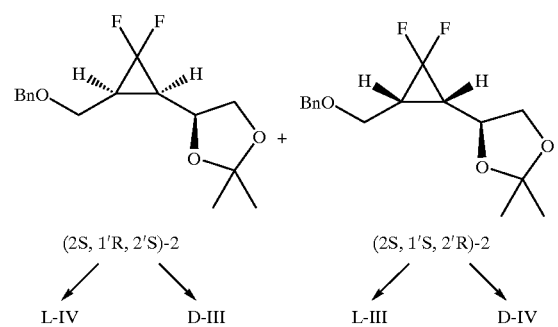

(2S, 1'R, 2'S)-2          (2S, 1'S, 2'R)-2

L-IV    D-III              L-III    D-IV

Reaction scheme-2

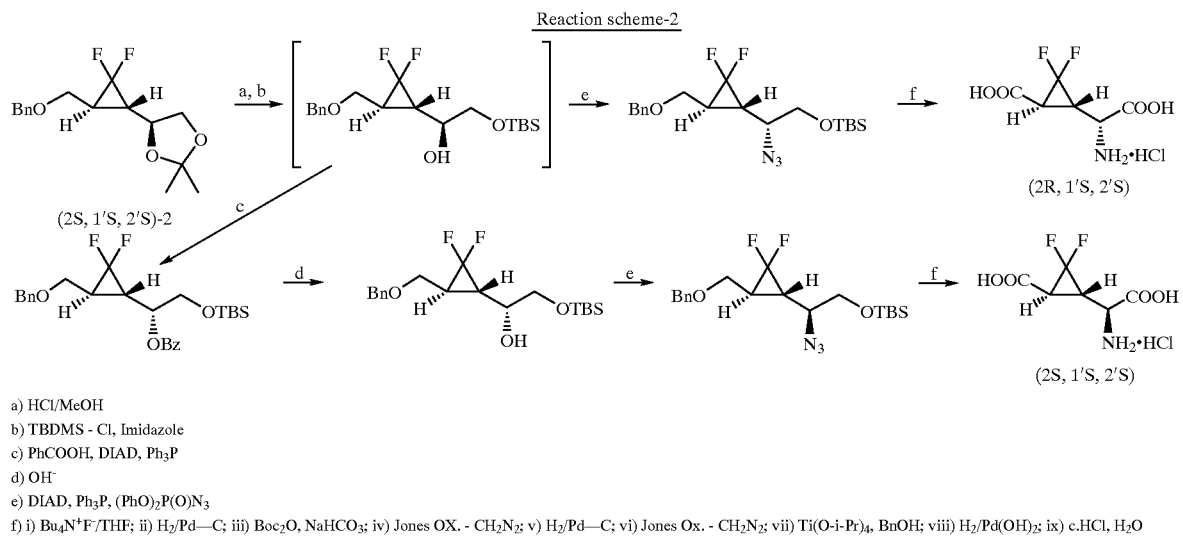

a) HCl/MeOH
b) TBDMS - Cl, Imidazole
c) PhCOOH, DIAD, Ph$_3$P
d) OH$^-$
e) DIAD, Ph$_3$P, (PhO)$_2$P(O)N$_3$
f) i) Bu$_4$N$^+$F$^-$/THF; ii) H$_2$/Pd—C; iii) Boc$_2$O, NaHCO$_3$; iv) Jones OX. - CH$_2$N$_2$; v) H$_2$/Pd—C; vi) Jones Ox. - CH$_2$N$_2$; vii) Ti(O-i-Pr)$_4$, BnOH; viii) H$_2$/Pd(OH)$_2$; ix) c.HCl, H$_2$O The preparation examples of the cyclopropylglycine derivatives of the invention are described below. In the manners of the following examples, the derivatives other than those mentioned below can be easily also prepared.

EXAMPLE 1

Preparation of [(2S,1'R,2'S)-2] and [(2S,1'S,2'R)-2] from [Z-1]—Reaction scheme-1

A diethyleneglycol dimethyl ether solution containing 7.5 g of (Z,4'S)-3-benzyloxy-1-(2',2'-dimethyl-1',3'-dioxolan-4'-yl)-1-propene [Z-1] was heated to 180° C. Into the heated solution, a diethyleneglycol dimethyl ether solution containing 45.8 g of sodium chlorodifluoroacetate was dropwise added for 10 hours. The resulting solution was heated at 180° C. for 1 hour, and then cooled. After an ice-water mixture was added, the solution was extracted with hexane. The extracted portion was washed with water, dried over magnesium sulfate, and concentrated under reduced pressure. The obtained residue was roughly purified by silica gel column chromatography (hexane: ethyl acetate=30:1, volume ratio), and then the optical isomers were separated by medium pressure chromatography (hexane:ethyl acetate=4:1, volume ratio), to obtain 2.6 g and 5.6 g, respectively, of the following products of [(2S,1'R,2'S)-2] and [(2S,1'S,2'R)-2].

[(2S,1'R,2'S)-2]: colorless oil
  $[\alpha]_D^{27.6}=-37.6$ (c 0.978, CHCl$_3$)
[(2S,1'S,2'R)-2] : colorless oil
  $[\alpha]_D^{28.0}=-35.6$ (c 0.999, CHCl$_3$)

EXAMPLE 2

Preparation of [(2S,1'S,2'S)-2] and [(2S,1'R,2'R)-2] from [E-1] —Reaction scheme-1

The procedure of Example 1 was repeated except for using 1.3 g of (E,4'S)-3-benzyloxy-1-(2',2'-dimethyl-1',3'-dioxolan-4'-yl)-1-propene [E-1] as the starting material, to prepare 0.76 g and 0.45 g, respectively, of the following products of [(2S,1'S, 2'S)-2] and [(2S,1'R,2'R)-2].

[(2S,1'S,2'S)-2]: colorless oil
  $[\alpha]_D^{26.0}=-20.9$ (c 1.00, CHCl$_3$)
[(2S,1'R,2'R)-2] : colorless oil
  $[\alpha]_D^{24.8}=+28.7$ (c 1.06, CHCl$_3$)

EXAMPLE 3

Preparation of (2R,1'S,2'S)-2-(2'-carboxy-3',3'-difluoro)cyclopropylglycine [D-II] and its esters—Reaction scheme-3

Reaction scheme-3

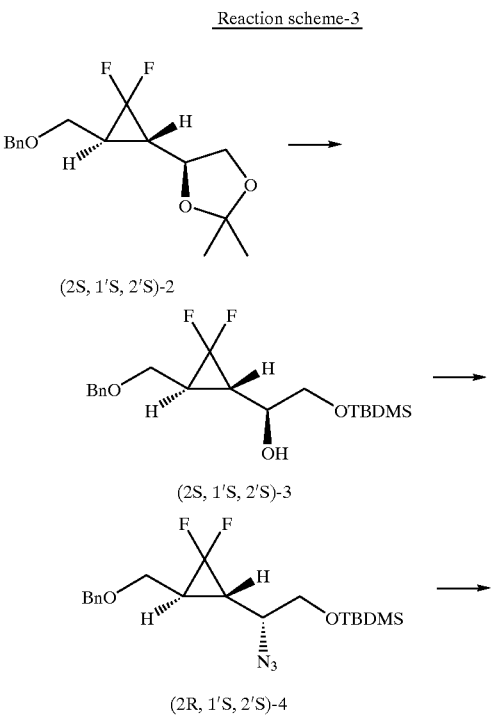

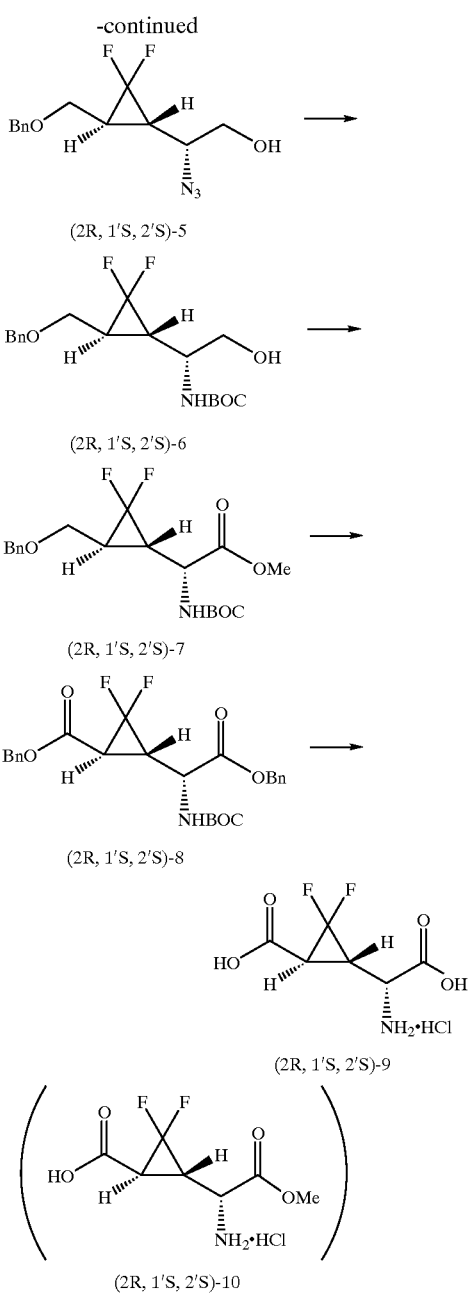

(1) Preparation of [(2S,1'S,2'S)-3] from [(2S,1'S, 2'S)-2]

Into 2 mL of a methanol solution containing 300 mg of [(2S,1'S,2'S)-2], 0.5 mL of 10% hydrochloric acid was dropwise added and caused to react for 6 hours at room temperature. The reaction mixture was concentrated under reduced pressure. After an aqueous saturated sodium hydrogencarbonate solution was added, the resultant solution was extracted with ethyl acetate. The organic portion was collected, washed with an aqueous saturated sodium chloride solution, dried over anhydrous magnesium sulfate, and concentrated under reduced pressure.

The residue was dissolved in 2 mL of N,N-dimethylformamide. Under argon atmosphere, 138.0 mg of imidazole was added to the solution, and then 167.0 mg of t-butyldimethylsilyl chloride (TBDMS-Cl) was added at 0° C., followed by stirring for 5 hours at room temperature. After an aqueous saturated ammonium chloride solution was added, the solution was extracted with diethyl ether. The organic portion was collected, washed with an aqueous saturated sodium chloride solution, dried over anhydrous magnesium sulfate, and concentrated under reduced pressure. The resultant residue was purified by silica gel column chromatography (hexane: ethyl acetate =15:1, volume ratio). From the eluent, 302.0 mg of the following product of [(2S,1'S, 2'S)-3] was obtained.

[(2S,1'S,2'S)-3]: colorless oil
$[\alpha]_D^{28.4}=-10.6$ (c 1.00, CHCl$_3$)

(2) Preparation of [(2R,1'S,2'S)-4] from [(2S,1'S, 2'S)-3]

Under argon atmosphere, 0.12 mL of diphenylphosphoryl azide and 87 µL of diethyl azodicarboxylate were added at 0° C. to 2 mL of a tetrahydrofuran solution containing 136 mg of [(2S,1'S,2'S)-3] and 165 mg of triphenylphosphine, and then the mixture was stirred for 6 hours at room temperature. To the resulting solution, an aqueous saturated sodium chloride solution was added. Then, the solution was extracted with diethyl ether;

The ether portion was collected, dried over anhydrous magnesium sulfate, and concentrated under reduced pressure. The residue was purified by silica gel column chromatography (hexane:ethyl acetate=15:1, volume ratio). From the eluent, 92 mg of the following product of [(2R, 1'S,2'S)-4] was obtained.

[(2R,1'S,2'S)-4]: colorless oil
$[\alpha]_D^{26.8}=-3.03$ (c 0.99, CHCl$_3$)

(3) Preparation of [(2R,1'S,2'S)-5] from [(2R,1'S, 2'S)-4]

To 3 mL of a tetrahydrofuran solution containing 92 mg of [(2R,1'S,2'S)-4], tetrabutylammonium fluoride was added at 0° C. The resulting solution was stirred for 3 hours. After an aqueous saturated sodium chloride solution was added, the solution was extracted with diethyl ether.

The ether portion was collected, dried over anhydrous magnesium sulfate, and concentrated under reduced pressure. The residue was purified by silica gel column chromatography (hexane:ethyl acetate=10:1, volume ratio). From the eluent, 65 mg of the following product of [(2R, 1'S,2'S)-5] was obtained.

[(2R,1'S,2'S)-5]: colorless oil
$[\alpha]_D^{26.0}=-42.4$ (c 0.97, CHCl$_3$)

(4) Preparation of [(2R,1'S,2'S)-6] from [(2R,1'S, 2'S)-5]

Under hydrogen atmosphere, 2 mL of an ethyl acetate suspension containing 2.1 g of [(2R,1'S,2'S)-5] and 5% Pd/C(charcoal) was stirred for 3 hours at room temperature under atmospheric pressure. The reaction mixture was filtered, and then concentrated under reduced pressure. The residue was dissolved in 18 mL of a mixture solvent of dioxane/water (2/1, volume ratio). To the solution, 3.1 g of sodium hydrogencarbonate and 3.5 g of di-t-butyl dicarbonate (Boc$_2$O) were added. The resulting mixture was stirred for 1 hour at room temperature. After an aqueous saturated sodium chloride solution was added, the solution was extracted with ethyl acetate. The organic portion was collected, dried over anhydrous magnesium sulfate, and concentrated under reduced pressure.

The residue was purified by silica gel column chromatography (hexane:ethyl acetate=3:2, volume ratio). From the eluent, 3.3 g of the following product of [(2R,1'S,2'S)-6] was obtained.

[(2R,1'S,2'S)-6]: colorless prisms
m.p.: 101.5–103.5° C.
$[\alpha]_D^{29.6}$=−19.99 (C 1.01, CHCl$_3$)

(5) Preparation of [(2R,1'S,2'S)-7] from [(2R,1'S,2'S)-6]

To 20 mL of an acetone solution containing 500 mg of [(2R,1'S,2'S)-6], 5 mL of Jones' reagent was added under chilling with ice. After one hour, 3 mL of isopropyl alcohol was added. The mixture was stirred for 30 minutes, and then water was added. The resulting solution was extracted with ethyl acetate, and then the organic portion was collected, dried over anhydrous magnesium sulfate, and concentrated under reduced pressure.

The residue was dissolved in 5 mL of diethyl ether, and then an ether solution containing diazomethane was added under chilling with ice. The reaction mixture was concentrated under reduced pressure, and the obtained residue was purified by silica gel column chromatography (hexane:ethyl acetate=5:1, volume ratio). From the eluent, 442 mg of the following product of [(2R,1'S,2'S)-7] was obtained.

[(2R,1'S,2'S)-7]: colorless prisms
m.p.: 59.0–61.0° C.
$[\alpha]_D^{29.2}$=−34.84 (c 0.528, CHCl$_3$)

(6) Preparation of [(2R,1'S,2'S)-8] from [(2R,1'S,2'S)-7]

Under hydrogen atmosphere, 1 mL of an ethyl acetate suspension containing 1.0 g of [(2R,1'S,2'S)-7] and palladium hydroxide was stirred for 5 hours at room temperature under atmospheric pressure. The reaction mixture was filtered, and concentrated under reduced pressure. The residue was treated in the #nner described in the (5) above, and then purified by silica gel column chromatography (hexane:ethyl acetate=1:1, volume ratio). The eluent was dissolved in 5 mL of benzyl alcohol, and then 0.87 mL of titanium tetraisopropoxide was added. After stirring for 3 hours at 70° C., the resulting solution was purified by silica gel column chromatography (hexane:ethyl acetate=20:1, volume ratio). The eluent was further purified by medium pressure chromatography (hexane:ethyl acetate=4:1, volume ratio), to prepare 393.0 mg of the following product of [(2R,1'S,2'S)-8].

[(2R,1'S,2'S)-8]: colorless prisms
m.p.: 114.5–116.5° C.
$[\alpha]_D^{28.0}$=+12.12 (c 1.006, CHCl$_3$)

(7) Preparation of [(2R,1'S,2'S)-9] from [(2R,1'S,2'S)-8]

Under hydrogen atmosphere, 0.5 mL of a methanol suspension containing 100 mg of [(2R,1'S,2'S)-8] and palladium hydroxide was stirred for 3 hours. The reaction mixture was filtered, and concentrated under reduced pressure. The residue was dissolved in 1.5 mL of a mixture solvent of tetrahydrofuran/water (1/1, vol/vol), and then 50 μL of 36% hydrochloric acid was added. Subsequently, the solution was stirred for 2 hours at 50° C.

The reaction mixture was concentrated under reduced pressure, and then purified by HPLC (H$_2$O) using a reversed phase column (ODS column). Thus, 18.7 mg of the following product of [(2R,1'S,2'S)-9] [hydrochloride of (2R,1'S,2'S)-2-(2'-carboxy-3',3'-difluoro)-cyclopropylglycine (D-II)p was obtained.

[(2R,1'S,2'S)-9]=hydrochloride of D-II
colorless prisms
m.p.: 160° C. (decomposed)
$[\alpha]_D^{25.6}$=−38.54 (c 0.890, H$_2$O)
IR (KBr) ν cm$^{-1}$: 3447, 3034, 2924, 1717, 1637, 1398, 1239, 1028, 948, 792.
$^1$H-NMR (400 MHz, D$_2$O)δ: 2.73 (1H, ddd, J=11.4, 10.9, 7.3 Hz), 2.97 (1H, dd, J=14.1, 7.2 Hz), 3.82 (1H, d, J=10.9 Hz).
$^{13}$C-NMR (100.6 MHz, D$_2$O)δ: 30.56 (dd, J=10.2, 9.3 Hz), 33.84 (dd, J=11.1, 10.9 Hz), 53.05, 113.08 (dd, J=292.3, 285.7 Hz), 171.89, 173.29.
$^{19}$F-NMR (376.5 MHz, D$_2$O)δ: −71.72 (1F, dd, J=158.2, 11.8 Hz), −70.05 (1F, dd, J=159.8, 13.7 Hz).

(8) Preparation of [(2R,1'S,2'S)-10] from [(2R,1'S,2'S)-7]

74.8 mg of [(2R,1'S,2'S)-7] was treated in the manner described in the above (6) for eliminating benzyl ether and performing Jones' oxidation. The obtained residue was dissolved in a mixture solvent of 10% hydrochloric acid/tetrahydrofuran (1/1 vol/vol), and then the solution was stirred for 1 hour at 50° C.

The reaction mixture was concentrated under reduced pressure, and then purified by HPLC (H$_2$O) using a reversed phase column (ODS column). Thus, 14.5 mg of the following product of [(2R,1'S,2'S)-10] (hydrochloric salt of monomethyl ester of (2R,1'S,2'S)-2-(2'-carboxy-3',3'-difluoro)cyclopropylglycine (D-II)] was obtained.

[(2R,1'S,2'S)-10]=hydrochloride of monomethyl ester of D-II:
colorless prisms
$[\alpha]_D^{26.0}$=−31.99 (c 1.45, H$_2$O)
$^1$H-NMR (300 MHz, D$_2$O)δ: 2.73 (1H, ddd, J=18.4, 11.4, 1.7 Hz), 2.97 (1H, dd, J=14.4, 7.5 Hz), 3.88 (3H, s), 4.14 (1H, d, J=11.0 Hz).
$^{13}$C-NMR (100.6 MHz, D$_2$O)δ: 29.78 (dd, J=11.5, 8.4 Hz), 33.87 (dd, J=10.9, 10.9 Hz), 52.24, 57.15, 112.86 (dd, J=292.1, 286.0 Hz), 171.05, 171.79.
$^{19}$F-NMR (376.5 MHz, D$_2$O)δ: −71.70 (1F, dd, J=160.6, 9.3 Hz), −70.01(1F, dd, J=157.9, 14.0 Hz).

EXAMPLE 4

Preparation of (2S,1'S,2'S)-2-(2'-carboxy-3',3'-difluoro)cyclopropylglycine [L-1] and its esters— Reaction scheme-4

Reaction scheme-4

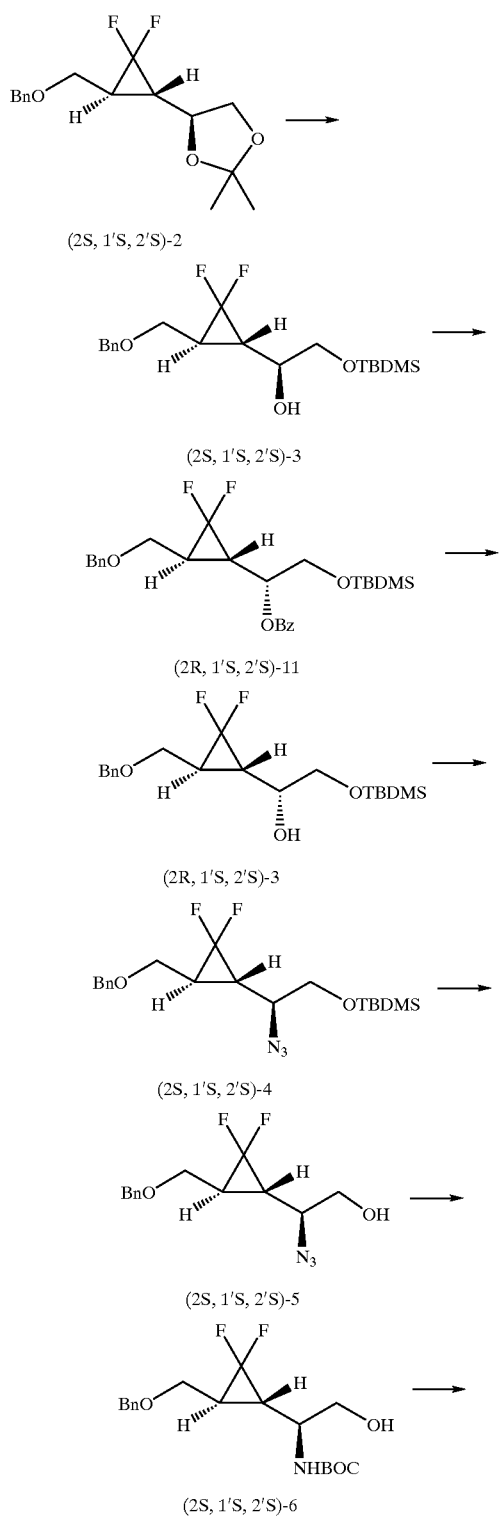

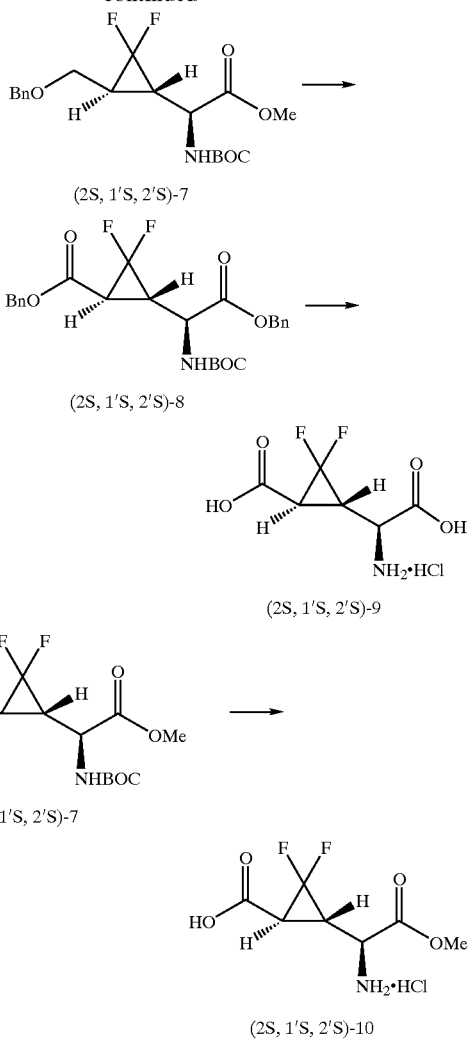

(1) Preparation of [(2R,1'S,2'S)-11] from [(2S,1'S, 2'S)-3]

To 10 mL of a tetrahydrofuran solution containing 3.0 g of [(2S,1'S,2'S)-3] and 4.0 g of triphenylphosphine, 2.1 mL of diethyl azodicarboxylate and 1.6 g of benzoic acid were added under chilling with ice. The mixture was then stirred for 2 hours at room temperature. After an aqueous saturated sodium chloride solution was added, the solution was extracted with diethyl ether. The organic portion was collected, dried over anhydrous sodium sulfate, and concentrated under reduced pressure.

The residue was purified by silica gel column chromatography (hexane:ethyl acetate=30:1, volume ratio). From the eluent, 3.5 g of the following product of [(2R,1'S,2'S)-11] was obtained.

[(2R,1'S,2'S)-11]: colorless oil
$[\alpha]_D^{25.6}$=+3.00 (c 1.000, $CHCl_3$)

(2) Preparation of [(2R,1'S,2'S)-3] from [(2R,1'S, 2'S)-11]

5 mL of an aqueous 1N-NaOH solution was added to 10 mL of a methanol solution containing 3.3 g of [(2R,1'S, 2'S)-11], and the resulting solution was stirred for 6 hours at room temperature. The solution was then concentrated under reduced pressure. After water was added to the residue, the solution was extracted with diethyl ether.

The organic portion was collected, dried over anhydrous magnesium sulfate, and concentrated under reduced pressure. The residue was purified by silica gel column chromatography (hexane:ethyl acetate=15:1, volume ratio). From the eluent, 1.7 g of the following product of [(2R,1'S, 2'S)-3] was obtained.

[(2R,1'S,2'S)-3]: colorless oil
  $[\alpha]_D^{24.4}=-16.89$ (c 1.006, CHCl$_3$)

(3) Preparation of [(2S,1'S,2'S)-9] from [(2R,1'S, 2'S)-3]

The [(2R,1'S,2'S)-3] obtained in the (2) above was treated in the manners described in the (2) to (7) of Example 3, to prepare the following product of [(2S,1'S,2'S)-9] (hydrochloride of (2S,1'S,2'S)-2-(2'-carboxy-3',3'-difluoro) cyclopropylglycine [L-I]).

[(2S,1'S,2'S)-9]=hydrochloride of L-I:
  colorless prisms
  m.p.: 155° C. (decomposed)
  $[\alpha]_D^{24.0}=+50.64$ (c 1.398, H$_2$O)
  IR (KBr) ν cm$^{-1}$: 3414, 3061, 1712, 1616, 1477, 1226, 1040, 737, 620.
  $^1$H-NMR (400 MHz, D$_2$O)δ: 2.78 (1H, ddd, J=13.0, 10.8, 7.5 Hz), 2.86 (1H, dd, J=14.2, 7.5 Hz), 3.92 (1H, d, J=10.7 Hz).
  $^{13}$C-NMR (100.6 MHz, D$_2$O)δ: 30.88 (dd, J=12.0, 8.9 Hz), 33.29 (dd, J=11.1, 10.9 Hz), 53.20, 113.26 (dd, J=289.6, 286.3 Hz), 171.77, 172.89.
  $^{19}$F-NMR (376.5 MHz, D$_2$O)δ: -70.35 (1F, dd, J=157.9, 13.1 Hz), -67.51 (1F, dd, J=156.9, 12.8 Hz).

(4) Preparation of [(2S,1'S,2'S)-10] from [(2R,1'S, 2'S)-3]

The [(2R,1'S,2'S)-3] obtained in the (2) above was treated in the manner described in the (8) of Example 3, to prepare the following product of [(2S,1'S,2'S)-10] (hydrochloride of monomethyl ester of (2S,1'S,2'S)-2-(2'-carboxy-3',3'-difluoro)cyclopropylglycine [L-I]).

[(2S,1'S,2'S)-10]=hydrochloride of monomethyl ester of L-I:
  colorless prisms
  $[\alpha]_D^{24.8}=+52.88$ (c 1.49, H$_2$O)
  $^1$H-NMR (300 MHz, D$_2$O)δ: 2.60–2.80 (2H, m), 3.91 (3H, s), 4.16 (1H, d, J=10.7 Hz).
  $^{13}$C-NMR (75.5 MHz, D$_2$O)δ: 29.94 (dd, J=13.0, 8.3 Hz), 33.38 (dd, J=11.1, 10.8 Hz), 53.39, 57.08, 112.73 (dd, J=290.0, 286.2 Hz), 170.61, 171.43.
  $^{19}$F-NMR (376.5 MHz, D$_2$O)δ: -70.65 (1F, dd, J=160.7, 13.0 Hz), -67.81 (1F, dd, J=157.4, 13.4 Hz).

EXAMPLE 5

Preparation of (2R,1'R,2'R)-2-(2'-carboxy-3',3'-difluoro)cyclopropylglycine [D-1]—Reaction scheme-5

Reaction scheme-5

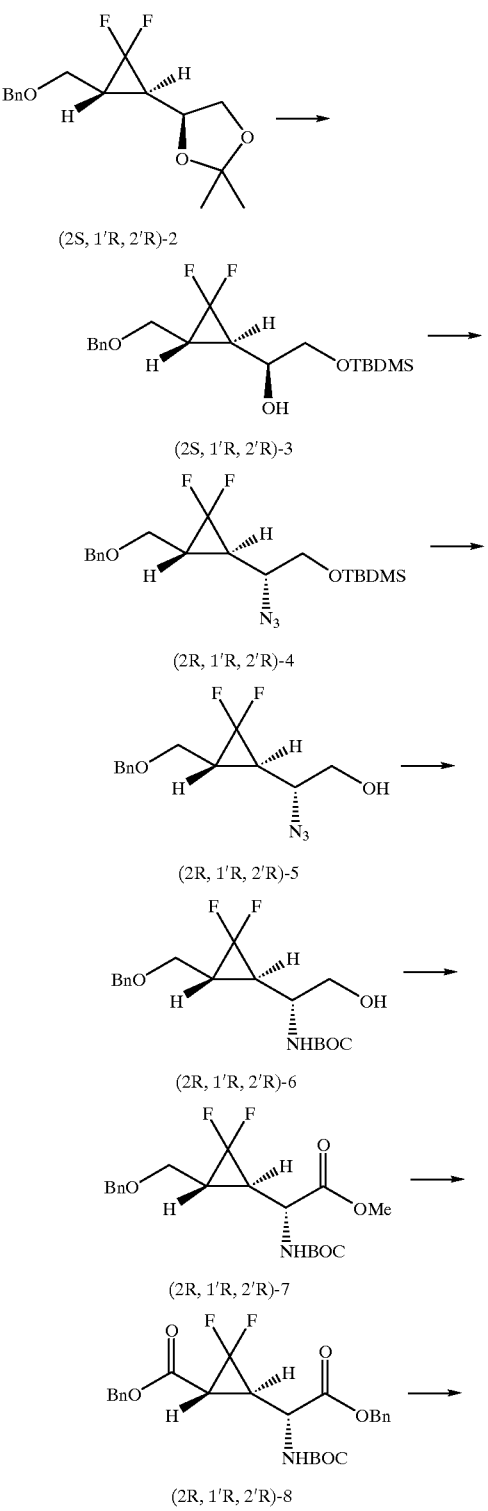

15
-continued

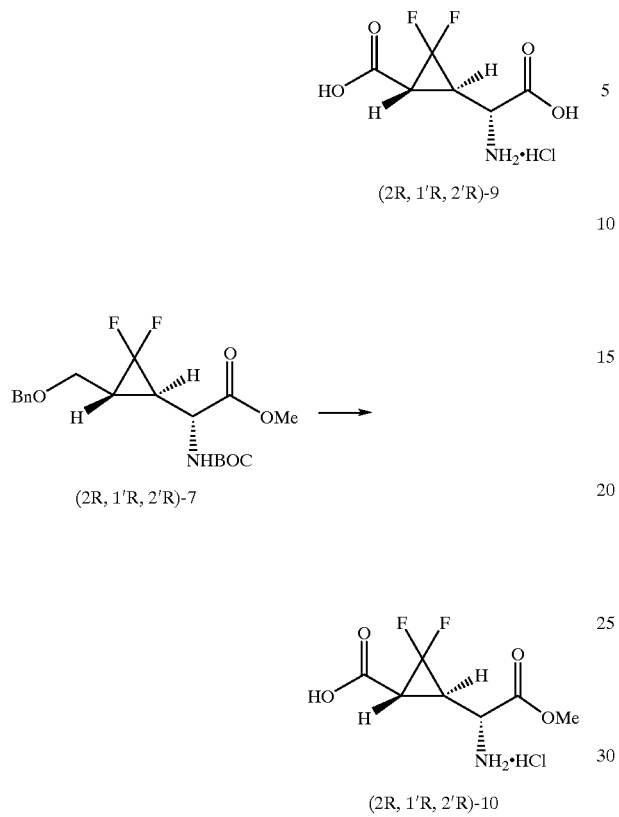

(1) Preparation of [(2R,1'R,2'R)-9] from [(2S,1'R, 2'R)-2]

[(2S,1'R,2'R)-2] was treated in the manners described in the (1) to (7) of Example 3, to prepare the following product of [(2R,1'R,2'R)-9] (hydrochloride of (2R,1'R,2'R)-2-(2'-carboxy-3',3'-difluoro)cyclopropylglycine [D-I]).

[(2R,1'R,2'R)-9]=hydrochloride of D-I:
colorless prisms
m.p.: 153° C. (decomposed)
$[\alpha]_D^{27.6}$=−47.49 (c 0.88, $H_2O$)
IR (KBr) ν $cm^{-1}$: 3424, 3035, 1721, 1638, 1477, 1212, 1045, 738, 622.
$^1$H-NMR (400 MHz, $D_2O$)δ: 2.72 (1H, ddd, J=13.2, 10.8, 7.6 Hz), 2.80 (1H, dd, J=14.4, 7.5 Hz), 3.81 (1H, d, J=10.7 Hz).
$^{13}$C-NMR (100.6 MHz, $D_2O$)δ: 31.24 (dd, J=11.8, 8.9 Hz), 33.78 (brt), 53.76, 113.52 (dd, J=289.0, 286.0 Hz), 172.37, 173.58.
$^{19}$F-NMR (376.5 MHz, $D_2O$)δ: −70.11 (1F, dd, J=157.4, 13.3 Hz), −67.44 (1F, dd, J=157.4, 15.9 Hz).

16
EXAMPLE 6

Preparation of (2S,1'R,2'R)-2-(2'-carboxy-3',3'-difluoro)cyclopropylglycine [L-II] and its esters—Reaction scheme-6

Reaction scheme-6

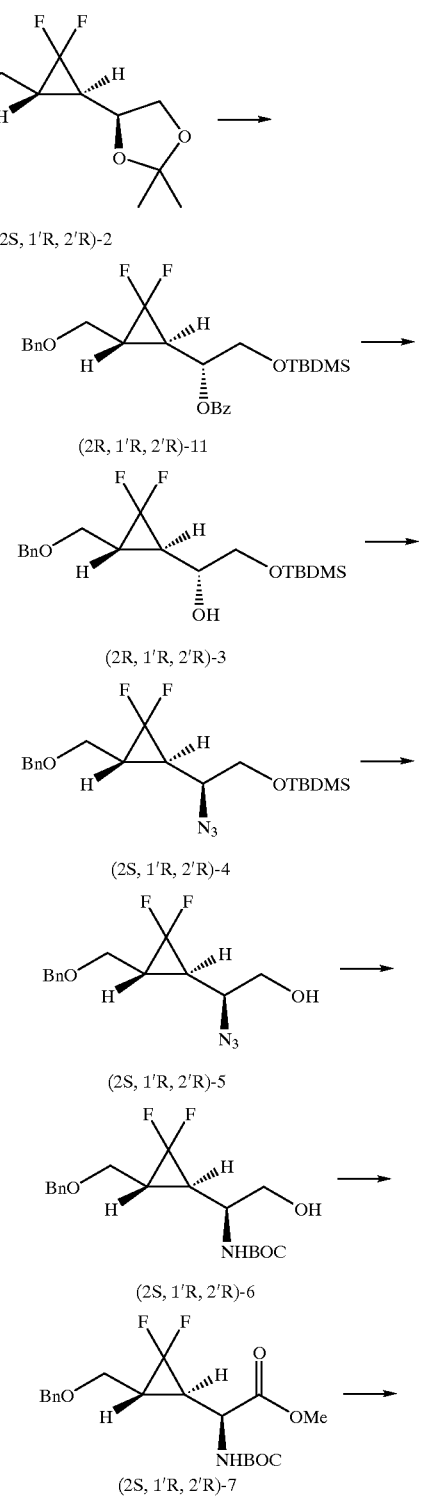

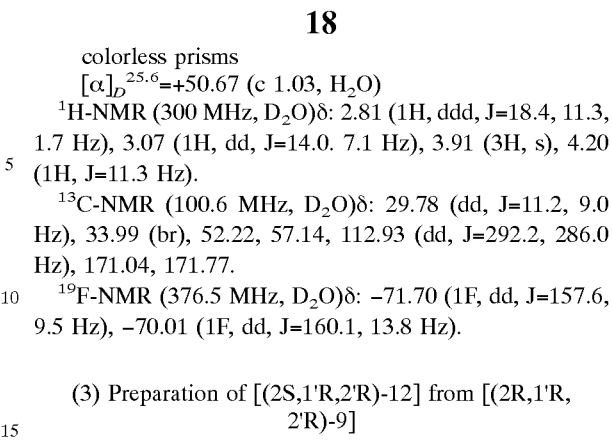

(2S, 1'R, 2'R)-8

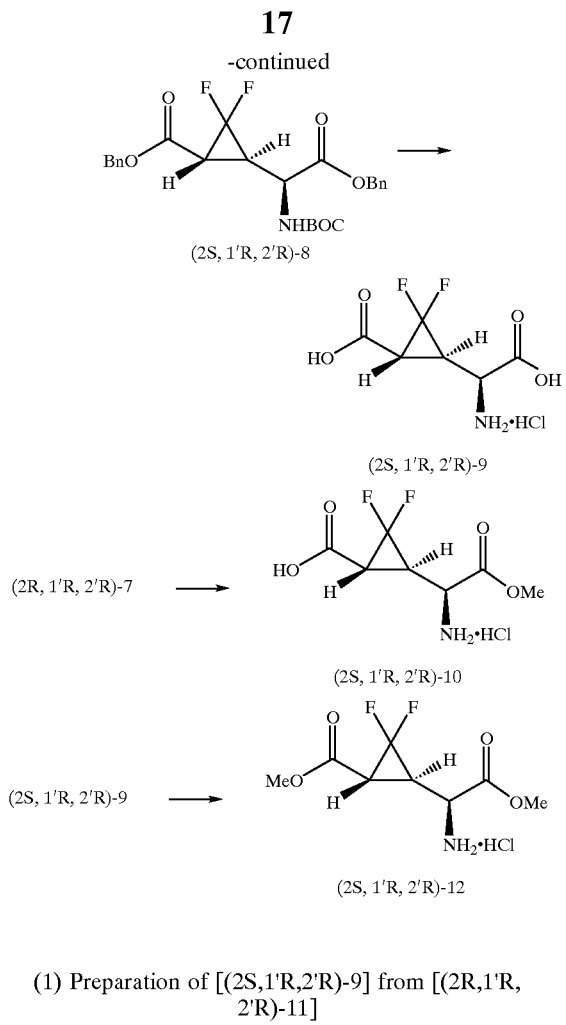

(2S, 1'R, 2'R)-9

(2R, 1'R, 2'R)-7 →

(2S, 1'R, 2'R)-10

(2S, 1'R, 2'R)-9 →

(2S, 1'R, 2'R)-12

(1) Preparation of [(2S,1'R,2'R)-9] from [(2R,1'R, 2'R)-11]

In the manner described in Example 4, the following product of [(2S,1'R,2'R)-9] (hydrochloride of (2S,1'R, 2'R)-2-(2'-carboxy-3',3'-difluoro)cyclopropylglycine [L-III] was prepared.

[(2S,1'R,2'R)-9]=hydrochloride of L-II:
  colorless prisms
  m.p.: 165° C. (decomposed)
  $[\alpha]_D^{24.0}$=+40.68 (c 0.870, H$_2$O)
  IR (KBr) ν cm$^{-1}$: 3209, 3046, 2928, 1716, 1646, 1387, 1226, 1028, 950, 784.
  $^1$H-NMR (400 MHz, D$_2$O)δ: 2.67 (1H, dddd, J=11.6, 10.9, 7.3, 1.6 Hz), 2.90 (1H, dd, J=14.3, 7.3 Hz), 3.72 (1H, d, J=10.9 Hz).
  $^{13}$C-NMR (100.6 MHz, D$_2$O)δ: 30.66 (dd, J=10.0, 9.5 Hz), 34.12 (dd, J=10.8, 10.6 Hz), 53.29, 113.21 (dd, J=291.9, 285.7 Hz), 172.21, 173.64.
  $^{19}$F-NMR (376.5 MHz, D$_2$O)δ: −71.73 (1F, dd, J=160.8, 12.7 Hz), −70.07 (1F, dd, J=159.7, 13.6 Hz).

(2) Preparation of [(2S,1'R,2'R)-10] from [(2R,1'R, 2'R)-7]

In the manner described in Example 4, the following product of [(2S,1'R,2'R)-10] (hydrochloride of monomethyl ester of (2S,1'R,2'R)-2-(2'-carboxy-3',3'-difluoro)cyclopropylglycine [L-II]) was prepared.

[(2S,1'R,2'R)-9]=hydrochloride of monomethyl ester of L-II:
  colorless prisms
  $[\alpha]_D^{25.6}$=+50.67 (c 1.03, H$_2$O)
  $^1$H-NMR (300 MHz, D$_2$O)δ: 2.81 (1H, ddd, J=18.4, 11.3, 1.7 Hz), 3.07 (1H, dd, J=14.0. 7.1 Hz), 3.91 (3H, s), 4.20 (1H, J=11.3 Hz).
  $^{13}$C-NMR (100.6 MHz, D$_2$O)δ: 29.78 (dd, J=11.2, 9.0 Hz), 33.99 (br), 52.22, 57.14, 112.93 (dd, J=292.2, 286.0 Hz), 171.04, 171.77.
  $^{19}$F-NMR (376.5 MHz, D$_2$O)δ: −71.70 (1F, dd, J=157.6, 9.5 Hz), −70.01 (1F, dd, J=160.1, 13.8 Hz).

(3) Preparation of [(2S,1'R,2'R)-12] from [(2R,1'R, 2'R)-9]

10 mg of the [(2R,1'R,2'R)-9] obtained in the above (1) was dissolved in a mixture solvent of diethyl ether/methanol (1/1, vol/vol), and then an ether solution containing diazomethane was added. After the resulting solution was concentrated under reduced pressure, 10% hydrochloric acid was added. The obtained mixture was again concentrated under reduced pressure, to prepare 11.2 mg of the following product of [(2S,1'R,2'R)-12] (hydrochloride of dimethyl ester of (2S,1'R,2'R)-2-(2'-carboxy-3',3'-difluoro) cyclopropylglycine [L-II]).

[(2S,1'R,2'R)-12]=hydrochloride of dimethyl ester of L-II:
  colorless prismatic crystals
  $^1$H-NMR (400 MHz, D$_2$O)δ: 2.88 (1H, dd, J=18.6, 11.3 Hz), 3.18 (1H, dd, J=13.6, 7.3 Hz), 3.83 (3H, s), 3.90 (3H, s), 4.21 (1H, J=11.1 Hz).
  $^{13}$C-NMR (75.5 MHz, D$_2$O)δ: 29.56 (dd, J=8.9, 8.5 Hz), 33.07 (dd, J=12.5, 10.2 Hz), 51.99, 56.29, 57.02, 112.90 (dd, J=292.0, 286.6 Hz), 170.13, 170.71.
  $^{19}$F-NMR (376.5 MHz, D$_2$O)δ: −71.80 (1F, dd, J=161.1, 12.9 Hz), −70.15 (1F, dd, J=160.7, 13.1 Hz).

EXAMPLE 7

Preparation of (2R,1'R,2'S)-2-(2'-carboxy-3',3'-difluoro)cyclopropylglycine [D-III]—Reaction scheme-7

Reaction scheme-7

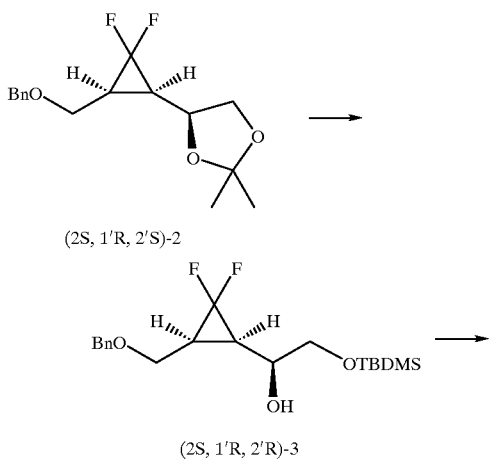

(2S, 1'R, 2'S)-2

(2S, 1'R, 2'R)-3

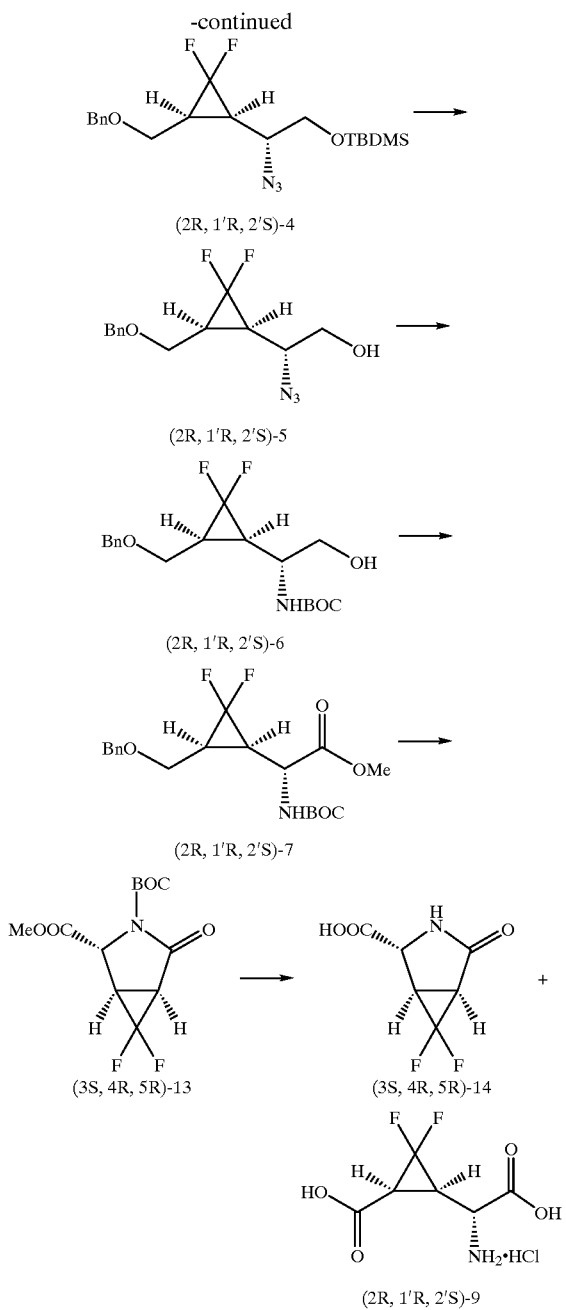

(1) Preparation of [(2R,1'R,2'S)-7] from [(2S,1'R, 2'S)-2]

[(2S,1'R,2'S)-2] was treated in the manner described in Example 3, to prepare [(2R,1'R,2'S)-7] as a colorless oil.

(2) Preparation of [(3S,4R,5R)-13] from [(2R,1'R, 2'S)-7]

Under hydrogen atmosphere, 1 mL of a methanol suspension containing 125 mg of [(2R,1'R,2'S)-7] and 5% Pd/C was stirred for 2 hours at room temperature under atmospheric pressure. The reaction mixture was filtered, and then concentrated under reduced pressure. The residue was dissolved in 5 mL of acetone, and then Jones' reagent was added. After stirring for 30 minutes, isopropyl alcohol was dropwise added. The solution was further stirred for 30 minutes, and an aqueous saturated sodium chloride solution was added. The resultant solution was extracted with diethyl ether, and the organic portion was collected, dried over anhydrous magnesium sulfate, and concentrated under reduced pressure. The residue was purified by silica gel column chromatography (hexane:ethyl acetate=5:1, volume ratio). From the eluent, 60 mg of ((3S,4R,5R)-13] was obtained as a colorless oil.

(3) Preparation of [(3S,4R,5R)-14] and [(2R,1'R, 2'S)-9] from [(3S,4R,5R)-13]

4 mL of 1N hydrochloric acid was added to 33 mg of [(3S,4R,5R)-13], and the mixture was stirred for 5 hours at 60° C. The reaction mixture was concentrated under reduced pressure, and then purified by HPLC ($H_2O$) using a reversed phase column (ODS column). Thus, 7.9 mg and 7.6 mg, respectively, of the following products of [(3S,4R,5R)-14] and [(2R,1'R, 2'S)-9] (hydrochloride of (2R,1'R,2'S)-2-(2'-carboxy-3',3'-difluoro)cyclopropylglycine [D-III] were obtained.

[(3S,4R,5R)-14] : colorless prisms
$^1$H-NMR (400 MHz, $D_2O$)δ: 3.00 (3H, dd, J=11.7, 8.2 Hz), 3.14 (1H, dd, J=10.9, 8.2 Hz), 4.58 (1H, s).
$^{13}$C-NMR (100.6 MHz, $D_2O$)δ: 30.18 (dd, J=12.9, 12.8 Hz), 32.84 (dd, J=13.7, 13.4 Hz), 56.81, 112.11 (dd, J=292.5, 278.2 Hz), 175.15, 176.05.
$^{19}$F-NMR (376.5 MHz, $D_2O$)δ: −84.26 (1F, d, J=157.1 Hz), −64.32 (1F, ddd, J=157.0, 12.6, 9.2 2 Hz).

[(2R,1'R,2'S)-9]=hydrochloride of D-III:
colorless prisms
$[α]_D^{25.0}$+17.34 (c 0.830, $H_2O$)
IR (KBr) ν cm$^{-1}$: 3422, 3038, 1721, 1627, 1471, 1400, 1225, 1045, 975, 710.
$^1$H-NMR (300 MHz, $D_2O$)δ: 2.61 (1H, ddd, J=11.8, 11.7, 11.6 Hz), 3.01 (1H, dd, J=12.6, 11.4 Hz), 4.55 (1H, d, J=11.3 Hz).
$^{13}$C-NMR (75.5 MHz, $D_2O$)δ: 29.12 (dd, J=11.7, 8.9 Hz), 31.25 (dd, J=10.6, 8.0 Hz), 50.46, 112.5 (dd, J=292.9, 282.9 Hz), 171.60, 173.44.
$^{19}$F-NMR (376.5 MHz, $D_2O$)δ: −79.04 (1F, d, J=159.1 Hz), −59.05 (1F, ddd, J=157.0, 13.1, 1 3.0 Hz).

EXAMPLE 8

Preparation of (2S,1'R,2'S)-2-(2'-carboxy-3',3'-difluoro) cyclopropylglycine [L-IV]—Reaction scheme-8

Reaction scheme-8

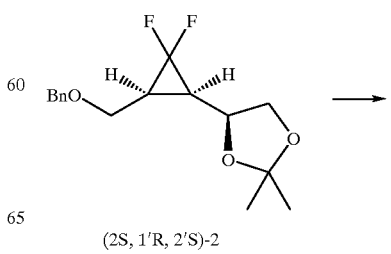

(2S, 1'R, 2'S)-2

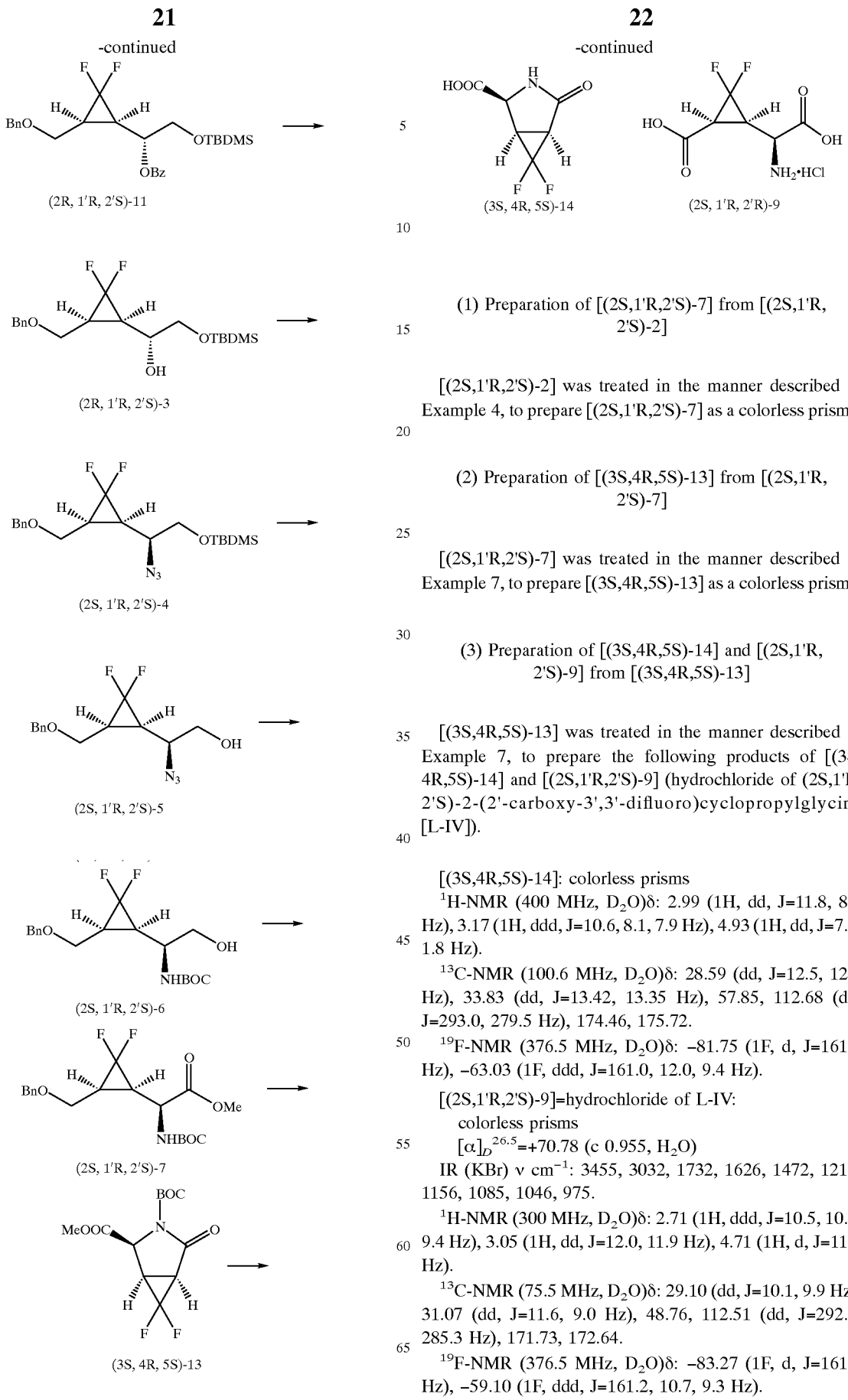

(1) Preparation of [(2S,1'R,2'S)-7] from [(2S,1'R,2'S)-2]

[(2S,1'R,2'S)-2] was treated in the manner described in Example 4, to prepare [(2S,1'R,2'S)-7] as a colorless prisms.

(2) Preparation of [(3S,4R,5S)-13] from [(2S,1'R,2'S)-7]

[(2S,1'R,2'S)-7] was treated in the manner described in Example 7, to prepare [(3S,4R,5S)-13] as a colorless prisms.

(3) Preparation of [(3S,4R,5S)-14] and [(2S,1'R,2'S)-9] from [(3S,4R,5S)-13]

[(3S,4R,5S)-13] was treated in the manner described in Example 7, to prepare the following products of [(3S,4R,5S)-14] and [(2S,1'R,2'S)-9] (hydrochloride of (2S,1'R,2'S)-2-(2'-carboxy-3',3'-difluoro)cyclopropylglycine [L-IV]).

[(3S,4R,5S)-14]: colorless prisms
$^1$H-NMR (400 MHz, D$_2$O)δ: 2.99 (1H, dd, J=11.8, 8.5 Hz), 3.17 (1H, ddd, J=10.6, 8.1, 7.9 Hz), 4.93 (1H, dd, J=7.4, 1.8 Hz).
$^{13}$C-NMR (100.6 MHz, D$_2$O)δ: 28.59 (dd, J=12.5, 12.4 Hz), 33.83 (dd, J=13.42, 13.35 Hz), 57.85, 112.68 (dd, J=293.0, 279.5 Hz), 174.46, 175.72.
$^{19}$F-NMR (376.5 MHz, D$_2$O)δ: −81.75 (1F, d, J=161.1 Hz), −63.03 (1F, ddd, J=161.0, 12.0, 9.4 Hz).

[(2S,1'R,2'S)-9]=hydrochloride of L-IV:
colorless prisms
$[\alpha]_D^{26.5}$=+70.78 (c 0.955, H$_2$O)
IR (KBr) ν cm$^{-1}$: 3455, 3032, 1732, 1626, 1472, 1219, 1156, 1085, 1046, 975.
$^1$H-NMR (300 MHz, D$_2$O)δ: 2.71 (1H, ddd, J=10.5, 10.4, 9.4 Hz), 3.05 (1H, dd, J=12.0, 11.9 Hz), 4.71 (1H, d, J=11.5 Hz).
$^{13}$C-NMR (75.5 MHz, D$_2$O)δ: 29.10 (dd, J=10.1, 9.9 Hz), 31.07 (dd, J=11.6, 9.0 Hz), 48.76, 112.51 (dd, J=292.4, 285.3 Hz), 171.73, 172.64.
$^{19}$F-NMR (376.5 MHz, D$_2$O)δ: −83.27 (1F, d, J=161.3 Hz), −59.10 (1F, ddd, J=161.2, 10.7, 9.3 Hz).

EXAMPLE 9

Preparation of (2R,1'S,2'R)-2-(2'-carboxy-3',3'-difluoro)cyclopropylglycine [D-IV]—Reaction scheme-9

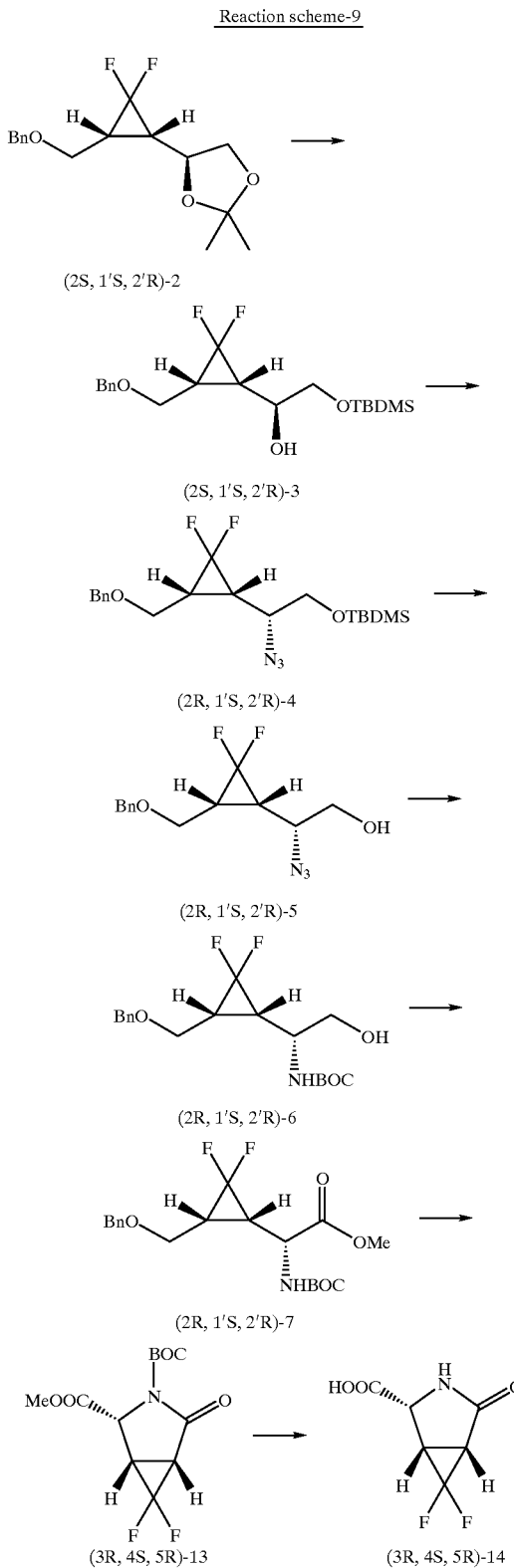

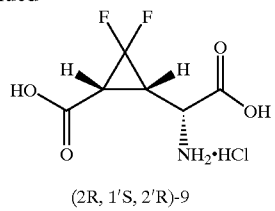

(2R, 1'S, 2'R)-9

In the manner described in Example 7, the following products of [(3R,4S,5R)-14] and [(2R,1'S,2'R)-9] (hydrochloride of (2R,1'S,2'R)-2-(2'-carboxy-3',3'-difluoro)cyclopropylglycine [D-IV]) were prepared.

[(3R,4S,5R)-14]: colorless prisms
$^1$H-NMR (400 MHz, D$_2$O)δ: 2.99 (1H, dd, J=11.9, 8.6 Hz), 3.17 (1H, dd, J=18.7, 8.1 Hz), 4.58 (1H, d, J=7.3 Hz).
$^{13}$C-NMR (100.6 MHz, D$_2$O)δ: 28.57 (dd, J=12.5, 12.4 Hz), 33.82 (dd, J=13.4, 13.3 Hz), 57.83, 112.67 (dd, J=293.0, 279.4 Hz), 174.44, 175.70.

[(2R,1'S,2'R)-9] =hydrochloride of D-IV:
colorless prisms
$[α]_D^{22.4}$=−67.99 (c 1.050, H$_2$O)
IR (KBr) ν cm$^{-1}$: 3432, 3039, 1731, 1636, 1471, 1219, 1155, 1084, 1047, 974.
$^1$H-NMR (400 MHz, D$_2$O)δ: 2.65 (1H, dddd, J=11.8, 11.7, 10.1, 2.5 Hz), 3.06 (1H, ddd, J=12.2, 12.1, 2.2 Hz), 4.58 (1H, d, J=11.4 Hz).
$^{13}$C-NMR (100.6 MHz, D$_2$O)δ: 29.27 (dd, J=10.3, 9.6 Hz), 31.50 (brt), 49.54 112.66 (dd, J=291.8, 283.9 Hz), 171.78, 173.25.
$^{19}$F-NMR (376.5 MHz, D$_2$O)δ: −83.24 (1F, d, J=161.4 Hz), −59.14 (1F, ddd, J=161.4, 11.7, 9.9 Hz).

EXAMPLE 10

Preparation of (2S,1'S,2'R)-2-(2'-carboxy-3', 3'-difluoro)cyclopropylglycine [L-III] —Reaction scheme-10

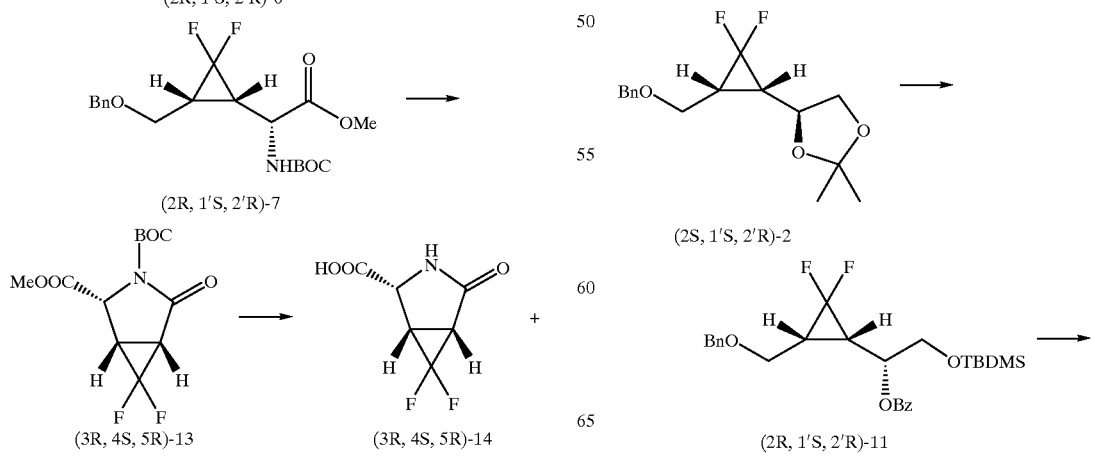

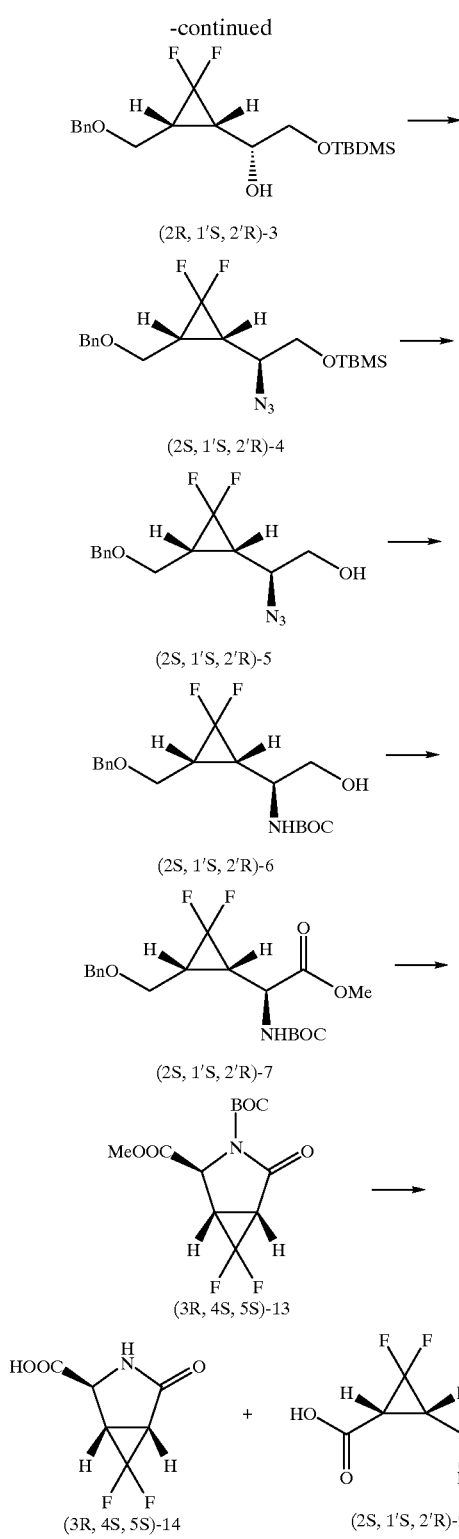

(2R, 1'S, 2'R)-3

(2S, 1'S, 2'R)-4

(2S, 1'S, 2'R)-5

(2S, 1'S, 2'R)-6

(2S, 1'S, 2'R)-7

(3R, 4S, 5S)-13

(3R, 4S, 5S)-14    (2S, 1'S, 2'R)-9

In the manner described in Example 8, the following products of [(3R,4S,5S)-14] and [(2S,1'S,2'R)-9] (hydrochloride of (2S,1'S,2'R)-2-(2'-carboxy-3',3'-difluoro) cyclopropylglycine [L-III]) were prepared.

[(3R,4S,5S)-14]: colorless prisms
$^1$H-NMR (400 MHz, D$_2$O)δ: 3.00 (1H, dd, J=11.7, 8.2 Hz), 3.14 (1H, dd, J=10.9, 8.3 Hz), 4.57 (1H, s).

$^{13}$C-NMR (100.6 MHz, D$_2$O)δ: 30.19 (dd, J=12.9, 12.6 Hz), 32.84 (t, J=13.4 Hz), 56.81, 112.05 (t, J=291.8 Hz), 175.16, 176.06.

[(2S,1'S,2'R)-9] =hydrochloride of L-III:
colorless prisms
$[α]_D^{25.4}$=−13.90 (c 0.820, H$_2$O)
IR (KBr) ν cm$^{-1}$: 3438, 3033, 1720, 1637, 1471, 1399, 1224, 1043, 974, 708.
$^1$H-NMR (300 MHz, D$_2$O)δ: 2.58 (1H, ddd, J=11.7, 11.5, 11.3 Hz), 2.99 (1H, dd, J=12.2, 10.7 Hz), 4.51 (1H, d, J=11.5 Hz).
$^{13}$C-NMR (75.5 MHz, D$_2$O)δ: 29.37 (dd, J=10.9, 9.5 Hz), 31.55 (dd, J=10.8, 10.2 Hz), 50.65, 112.77 (dd, J=292.7, 282.9 Hz), 171.81, 173.63.
$^{19}$F-NMR (376.5 MHz, D$_2$O)δ: −79.02 (1F, d, J=158.9 Hz), −59.03 (1F, ddd, J=157.0, 13.1, 12.5 Hz).

EXAMPLE 11

Preparation of (2S,1'S,2'S)-2-(2'-carboxy-3',3'-difluoro)cyclopropylglycine [L-I]—Reaction scheme-11

Reaction scheme-11

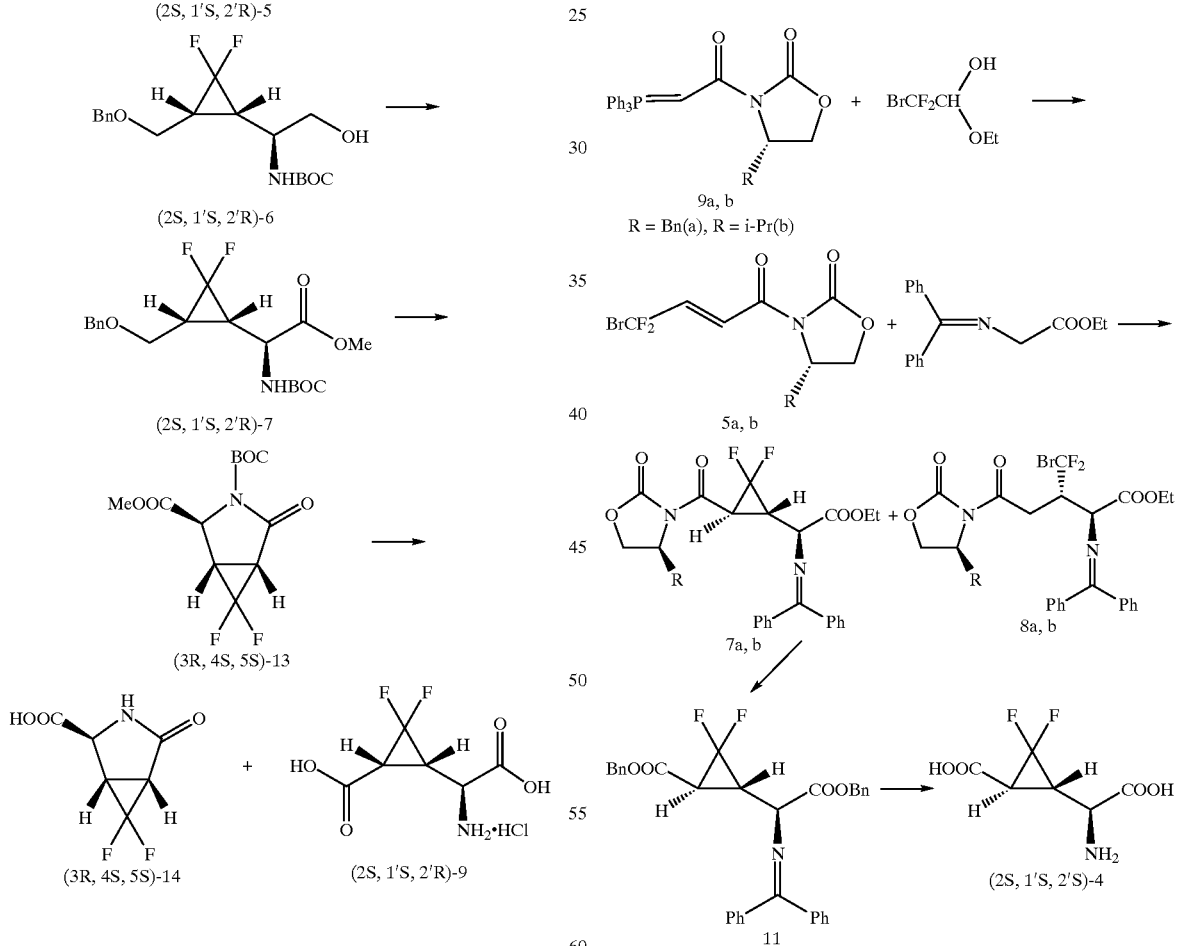

(1) Preparation of (4S)-3-[(E)-4'-bromo-4', 4'-difluoro-2'-butenoyl]-4-benzyl-2-oxazolidinone (Compound-5a)

Under argon atmosphere, 15 mL of an acetonitrile solution containing 3.7 g of (4S)-N-bromoacetyl-4-benzyl-2- oxazolidinone and 3.6 g of triphenylphosphine was stirred for two days at 50° C. After adding 6.5 mL of 2N-NaOH aqueous solution, the reaction mixture was extracted with ethyl ether. The organic portion was collected, dried over anhydrous magnesium sulfate, and concentrated under reduced pressure to obtain crude phosphorane-9a.

Independently, a mixture of 1.7 mL of ethyl bromodifluoroacetate and 14.7 mL of 0.93M DIBAL-H (diisobutylaluminum hydride hexane solution) in 10 mL of ethyl ether was stirred for 20 minutes at −78° C. To the mixture, 5 mL of methanol and 10 mL of 5% aqueous HCl were successively added. The resultant mixture was stirred for 10 minutes at room temperature, and then extracted with ethyl ether. The organic portion was collected, washed successively with an aqueous saturated sodium hydrogencarbonate solution and an aqueous saturated sodium chloride solution, dried over anhydrous magnesium sulfate, and concentrated under reduced pressure.

The residue and crude phosphorane 9a were dissolved in 38 mL of tetrahydrofuran (THF), and thus prepared solution was stirred for 5 hours at room temperature. Subsequently, the solvent was distilled off under reduced pressure, and the residue was purified by silica gel column chromatography to obtain 2.88 of (4S)-3-[(E)-4'-bromo-4',4'-difluoro-2'-butenoyl]-4-benzyl-2-oxazolidinone (Compound-5a) as a colorless oil.

(2) Preparation of (2S,1'S,2'S,4"S)-ethyl N-diphenylmethylidene-2-[2'-{(4"-benzyl-2"-oxazolidinon-3"-yl)-carbonyl}-3',3'-difluoro) cyclopropylglycinate (Compound-7a)

Under argon atmosphere, a mixture of 756 mg of ethyl N-(diphenylmethylidene)glycinate and LDA (lithium diisopropylamide), prepared from 0.47 mL of N,N-diisopropylamine and 1.87 mL of 1.65 M n-butyl lithium hexane solution, in 15 mL of dimethylformamide (DMF) was stirred for 15 minutes at −20° C. Independently, 926 mg of the above-prepared (4S)-3-[(E)-4'-bromo-4',4'-difluoro-2'-butenoyl]-4-benzyl-2-oxazolidinone (Compound-5a) was dissolved in 10 mL, of DMF, and the obtained solution was added to the mixture. The resulting mixture was stirred for 2 hours at the same temperature. After adding an aqueous saturated ammonium chloride solution to quench the reaction, the reaction mixture was extracted with ethyl ether. The organic portion was collected, washed with an aqueous saturated sodium chloride solution, dried over anhydrous magnesium sulfate, and concentrated under reduced pressure. The residue was purified by silica gel column chromatography (hexane:ethyl acetate=7:1, volume ratio), to prepare 758 mg of Compound-7a (colorless oil, yield: 54%) and 245 mg of Compound-8a (colorless oil, yield: 16%)

(3) Preparation of (2S,1'S,2'S)-2-(2'-carboxy-3', 3'-difluoro)cyclopropylglycine [L-I]

Under reduced pressure (40 mmHg), a mixture of 1 mL of benzyl alcohol and 154 mg of Ti(O-i-Pr)$_4$ was stirred for 30 minutes at room temperature. The obtained liquid and 100 mg of Compound-7a prepared above were mixed and stirred for 7 hours at 70° C. The reaction mixture was purified by silica gel column chromatography (hexane: ethyl acetate= 10:1, volume ratio), to obtain 87 mg of dibenzyl ester-11 (yield: 89%) as a cololess oil.

Under hydrogen atmosphere, 1 mL of a methanol suspension containing 87 mg of dibenzyl ester-11 and 5% Pd/C was stirred for 5 hours at room temperature. The reaction mixture was filtered, and to the filtrate was added water, then extracted with hexane. The aqueous portion was collected, and concentrated under reduced pressure to obtain a solid residue. The residue was washed with ethyl ether to obtain 31 mg of the following product of (2S,1'S,2'S)-2-(2'-carboxy-3',3'-difluoro)cyclopropylglycine [L-I].

L-I: colorless prisms
m.p.: 200° C. (decomposed)
$[\alpha]_D^{23.2}$=+39.4 (c 1.00, H$_2$O)
IR (KBr) ν cm$^{-1}$: 3106, 1621, 1530, 1476, 1393.
$^1$H-NMR (400 MHz, D$_2$O)δ: 2.72 (1H, m), 2.80 (1H, dd, J=15.0, 7.8 Hz), 3.81 (1H, d, J=10.7 Hz).
$^{13}$C-NMR (100.6 MHz, D$_2$O)δ: 31.3 (dd, J=11.6, 8.6 Hz), 34.1 (br), 54.2 (br), 113.7 (dd, J=288.2, 286.1 Hz), 172.7, 173.7.
$^{19}$F-NMR (376.5 MHz, D$_2$O)δ: −71.4 (1F, dd, J=157.6, 13.6 Hz), −69.0 (1F, dd, J=157.2, 14.8 Hz).

[Pharmacological Experiments]

(1) Action on metabotropic L-glutamate receptors (mGluR) of Group-I

Evaluation of depolarization activity

In accordance with Shinozaki's method [Shinozaki et al., Br. J. Pharmacol., 98, 1213–1224(1989)], the depolarization activities of the above-prepared compounds were measured using spinal specimen enucleated from neonatal rats.

With respect to each of the compounds of the invention [hydrochlorides of L-I to IV, and D-I to IV] and optical isomers of CCG [2-(carboxycyclopropyl)glycine, which was a known agonist for mGluR], the measurement was carried out in the following manner.

Under perfusing an artificial cerebrospinal fluid including 0.5 μM of tetrodotoxin, depolarization at the ventral root of the spinal cord was caused by the test compound, and extracellularly recorded. The measurement was repeated in the range of 10$^{-3}$ to 10$^{-7}$ M of the test compound, and thereby the minimal effective concentration (MEC) was estimated.

The activity of each compound was determined on the basis of the ratio of the MEC of the test compound to that of the corresponding optical isomer of COG. The results are set forth in Table 1.

TABLE 1

| | Ratio of the activity of each compound based on that of the corresponding optical isomer of CCG | | | |
|---|---|---|---|---|
| | I | II | III | IV |
| L | 3 | 0.3 | 2 | 1.5 |
| D | 1.5 | 0.1 | <0.1 | <0.01 |

TABLE 2

| | Minimal effective concentration ($\mu$M) of the corresponding optical isomer of CCG | | | |
|---|---|---|---|---|
| | I | II | III | IV |
| L | 2 | 200 | 100 | 0.3 |
| D | 3 | 0.1 | 300 | 5 |

When $3 \times 10^{-5}$ M of an NMDA antagonist (CPP [3-{(RS)-2-carboxypiperazin-4-yl}propyl-1-phosphoric acid] or D-AP5 [D(−)-2-amino-5-phosphonovaleric acid]) was added to the artificial cerebrospinal fluid, it was confirmed that the depolarization activities of L-I and L-II are hardly affected by the NMDA antagonist.

It was also confirmed that L-I causes NMDA-like depolarization at the magnitude of approx.1/33 based on that caused by known DCG-IV [(2S,1'R,2'R,3'R)-2-(2,3-dicarboxycyclopropyl)glycine]. This means that the depolarization caused by L-I is practically negligible.

When 100 $\mu$M of an NMDA antagonist (D-AP5) and 100 $\mu$M of a non-NMDA antagonist (CNQX [6-cyano-7-nitroquinoxaline-2,3-dione]) were incorporated into the artificial cerebrospinal fluid, it was confirmed that the depolarization activities of L-I and -II are hardly reduced by these antagonists although those of L-III, L-IV and D-I to D-IV are inhibited.

Furthermore, when 1 mM of an antagonist for mGluR of Group I [MCPG, (RS)-α-methyl-4-carboxyphenylglycine] was incorporated into the artificial cerebrospinal fluid, it was confirmed that the depolarization activities of L-I and L-II are inhibited by the antagonist.

(2) Action on metabotropic L-glutamate receptors (mGluRs) of Group-II

Evaluation of the inhibitory activity on monosynaptic reflex

In accordance with Ohtsuka's method [Ohtsuka M., Seitai no Kagaku, 36(4), 325–327], the monosynaptic reflex inhibitory activities of the above-prepared compounds were measured using spinal cord specimen enucleated from neonatal rats in the following manner.

The spinal cord was enucleated together with the vertebral column from a neonatal Wistar rat anesthetized with ether, and soaked in an artificial cerebrospinal fluid saturated with a mixed gas of $O_2$ and $CO_2$ (95%: 5%). In the artificial cerebrospinal fluid, the spinal cord in the vertebral column was sectioned under a microscope to prepare a spinal cord specimen having the ventral and dorsal roots of L3 to L5. The prepared sample was set in the perfusion system, and then the artificial cerebrospinal fluid saturated with the above mixed gas was made to flow.

The test compound was added into the perfusion liquid, and the monosynaptic reflex was measured by the steps of giving a pulse to the dorsal root through an suction electrode, recording the reflex potential at the ventral root, and observing a rapidly responding spike (corresponding to the monosynaptic reflex) and delayed depolarization with nonsynchronous potential drift. The measurement was repeated except that the concentration of the test compound was varied, and thereby the minimal effective concentration (MEC) was estimated.

This experiment revealed that the MEC of L-CCG-I (a known agonist for mGluR) is 0.2 $\mu$M and that the cyclopropylglycine derivative L-I of the invention inhibits the spinal monosynaptic reflex three times as strong as L-CCG-I.

Further, the measurement was repeated except that 0.3 mM of an antagonist for mGluR of Group II [MCCG-I, (2S,3S, 4S)-α-methyl-2-(2-carboxycyclopropyl)glycine] was incorporated into the artificial cerebrospinal fluid. By this measurement, it was confirmed that the inhibitory activities on the monosynaptic reflex of L-I and L-II are vanished by the antagonist.

(3) Summary of pharmacological actions belonging to cyclopropylglycine derivatives of the invention 1) The depolarization activity of L-I was slightly (5%) inhibited by 100 $\mu$M of D-AP5 (NMDA antagonist), hardly inhibited by CNQX (non-NMDA antagonist), and completely inhibited by 1 mM of MCPG (antagonist for mGluR of Group I).

Further, L-I reduced the spinal monosynaptic reflex, but this action was inhibited by MCCG (antagonist for mGluR of Group II).

Those results of the experiments indicate that L-I works as an agonist for mGluRs of both Groups-I and -II, and the minimal effective concentration (MEC) suggests that the agonistic effect for Group-II is predominant to that for Group-I.

2) L-II was insensitive to CNQX (non-NMDA antagonist), and hence is presumed to be an agonist for mGluR of Group-I.

3) L-III, L-IV and all D-isomers are presumed to be NMDA agonists.

4) L-III lacks the activity for inhibiting the transporter for glutamic acid although L-CCG-III has that activity. [Folia Pharmacol. Jpn., No. 104, 177–187 (1994); Br. J. Pharmacol., 98, 1213–1224(1989)].

INDUSTRIAL APPLICABILITY

The cyclopropylglycine derivative of the invention, particularly (2S,1'S,2'S)-2-(2'-carboxy-3',3'-difluoro) cyclopropylglycine, has excellent characteristics as an agonist for metabotropic L-glutamate receptors, and is therefore supposed to be used as a sedative, an analgesic, an anesthetic enhancer, an anticonvulsant, and a remedy for various cerebral functional disorders (e.g., Huntington's disease, epilepsy, Parkinson's disease) caused by degeneration or ischemic death of neurons.

Further, the cyclopropylglycine derivative of the invention is usable for pharmaceutical studies to develop antagonists for L-glutamic acid receptors.

What is claimed is:

1. A cyclopropylglycine derivative having the following formula:

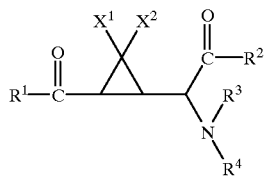

in which each of $R^1$ and $R^2$ independently represents a hydroxyl group or an alkoxy group having 1 to 6 carbon atoms, each of $R^3$ and $R^4$ independently represents a hydrogen atom or an alkyl group having 1 to 6 carbon atoms, and each of $X^1$ and $X^2$ independently represents a halogen atom.

2. The cyclopropylglycine derivative of claim 1, wherein each of $R^3$ and $R^4$ represents a hydrogen atom, and each of $X^1$ and $X^2$ represents a fluorine atom.

3. (2S,1'S,2'S)-2-(2'-carboxy-3',3'-difluoro) cyclopropylglycine.

4. An agonist for metabotropic L-glutamate receptors comprising, as an active compound, a cyclopropylglycine derivative having the following formula:

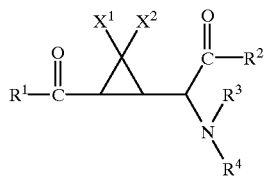

in which each of $R^1$ and $R^2$ independently represents a hydroxyl group or an alkoxy group having 1 to 6 carbon atoms, each of $R^3$ and $R^4$ independently represents a hydrogen atom or an alkyl group having 1 to 6 carbon atoms, and each of $X^1$ and $X^2$ independently represents a halogen atom.

5. The agonist for metabotropic L-glutamate receptors of claim 4 wherein each of $R^3$ and $R^4$ represents a hydrogen atom, and each of $X^1$ and $X^2$ represents a fluorine atom.

6. An agonist for metabotropic L-glutamate receptors comprising (2S,1'S,2'S)-2-(2'-carboxy-3', 3'-difluoro) cyclopropylglycine as an active compound.

7. A lactam derivative having the following formula:

(II)

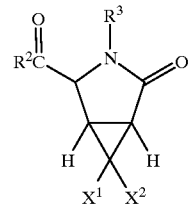

in which $R^2$ represents a hydroxyl group or an alkoxy group having 1 to 6 carbon atoms, $R^3$ represents a hydrogen atom or an alkyl group having 1 to 6 carbon atoms, and each of $X^1$ and $X^2$ independently represents a halogen atom.

* * * * *